(12) United States Patent
Terrero

(10) Patent No.: US 7,323,495 B2
(45) Date of Patent: *Jan. 29, 2008

(54) SYNTHETIC LACTONE FORMULATIONS AND METHOD OF USE

(75) Inventor: David Terrero, Ensanche Quisquella (DO)

(73) Assignee: Magnachem International Laboratories, Inc., Boca Raton, FL (US)

( * ) Notice: Subject to any disclaimer, the term of this patent is extended or adjusted under 35 U.S.C. 154(b) by 409 days.

This patent is subject to a terminal disclaimer.

(21) Appl. No.: 10/701,584

(22) Filed: Nov. 5, 2003

(65) Prior Publication Data

US 2005/0101663 A1   May 12, 2005

Related U.S. Application Data

(60) Provisional application No. 60/424,045, filed on Nov. 5, 2002.

(51) Int. Cl.
  *A61K 31/34*  (2006.01)
(52) U.S. Cl. ..................................... 514/473
(58) Field of Classification Search ................ 514/460, 514/473
  See application file for complete search history.

(56) References Cited

U.S. PATENT DOCUMENTS

| | | | |
|---|---|---|---|
| 3,210,377 | A | 10/1965 | Machleidt et al. |
| 4,001,425 | A | 1/1977 | Price, Jr. et al. |
| 4,613,613 | A | 9/1986 | Oguri et al. |
| 5,250,735 | A | 10/1993 | Wong et al. |
| 5,281,622 | A | 1/1994 | Wong et al. |
| 5,646,164 | A | 7/1997 | Tzeng et al. |
| 5,905,089 | A | 5/1999 | Hwang et al. |
| 5,962,460 | A | 10/1999 | Tzeng et al. |
| 5,977,169 | A | 11/1999 | Chrusciel et al. |
| 6,232,474 | B1 | 5/2001 | Brandenburg et al. |

FOREIGN PATENT DOCUMENTS

JP   2002037797   2/2002

OTHER PUBLICATIONS

Chen, et al., "α-Methylene-γ-butyrolactones: synthesis and vasorelaxing activity assay of coumarin, naphthalene, and quinolone derivatives," *Chem. Pharm. Bull.* 46(6): 962-965 (1998).

Fuchino, et al., "New sesquiterpene lactones from *Elephantopus mollis* and their leishmanicidal activities," *Planta Med* 67: 647-653 (2001).

Huang, et al., "Synthetic and cytotoxic studies of α-methyleneγ-butyrolactone bearing pyrimidines," *Kaohsiung J. Med. Sci.* 9: 707-711 (1993).

Kuhajda, et al., "Synthesis and antitumor activity of an inhibitor of fatty acid synthase," *Proc. Natl. Acad. Sci. USA* 97(7): 3450-3454 (2000).

Lee, et al., "Sesquiterpene antitumor agents: inhibitors of cellular metabolism," *Science* 196: 533-535 (1977).

Lee, et al., "Synthesis and anticancer evaluation of certain α-methylene-γ-(4-substituted phenyl)-g-butyrolactone bearing thymine, uracil, and 5-bramouracil," *Bioorg. & Med. Chem.* 9: 241-244 (1999).

Maria, et al., "Gastric anti-ulcer activity of several α,β-unsaturated carbonyl compounds in rats," *Biol. Pharm. Bull.* 23(5): 555-557 (2000).

Panda, et al., "Mechanism of action of alpha-methylene-gamma-lactone derivatives of substituted nucleic acid bases in tumour cells," *Chemotherapy* 35: 174-180 (1989).

Rodriguez, et al., "Biological activities of sesquiterpene lactones," *Phytochemistry* 15: 1573-1580 (1976).

Sanyal, et al., "New α-methylene-γ-lactone derivatives of substituted nucleic acid bases as potential anticancer agents," *J. Med. Chem.* 29(5): 595-599 (1986).

Schlewer, et al., "Synthesis of α-methylene-γ-butyrolactones: a structure-activity relationship study of their allergenic power," *J. Med. Chem.* 23: 1031-1038 (1980).

Spring, et al., "Annuithrin, a new biologically active germacranofide from *Helianthus annuus*," *Phytochemistry* 20(8): 1883-1885 (1981).

Willuhn, "*Arnica* flowers: pharmacology, toxicology, and analysis of the sesquiterpena lactones—their main active substance," in *Phytomedicines of Europe: Chemistry and Biological Activity* (Lawson, et al, eds.) Washington DC American Chemical Society, pp. 118-132 (1997).

*Primary Examiner*—Johann Richter
*Assistant Examiner*—Ebenezer Sackey
(74) *Attorney, Agent, or Firm*—Pabst Patent Group LLP

(57) ABSTRACT

Natural and synthetic compounds having a lactone structure methods for using and making the compounds have been disclosed. The compounds are useful as anti-bacterial, antifungal and anti-inflammatory agents, and for treating proliferation disorders such as melanoma, leukemia, breast cancer, lung cancer, ovarian cancer, colon cancer, esophagus cancer, liver cancer, and lymphatic cancer. The compounds are also effective for treatment or prevention of inflammatory diseases such as artherosclerosis, lung fibrosis, systemic lupus erythematosus, pancreatitis, sarcoidosis, glomerulitis, and organ transplant rejection. They are also effective for treatment or prevention of bacterial and fungal infections, including treatment of peptic ulcers, gastritis, dyspepsia and gastric cancer, gingivitis and periodontitis.

3 Claims, No Drawings

SYNTHETIC LACTONE FORMULATIONS AND METHOD OF USE

FIELD OF THE INVENTION

This application claims priority to U.S. Provisional Patent Application No. 60/424,045 filed Nov. 5, 2002.

The present inventions are generally in the fields of pharmaceutically active lactones, their pharmaceutical formulations, and method of use thereof, and methods for the synthetic preparation of chemically functionalized lactones useful therefor as anticancer, antiinfective and anti-inflammatory agents.

BACKGROUND OF THE INVENTION

Despite the development of many different compounds which are useful in the treatment of infection, cancer, and other disorders, there remains a need for the development of new compounds which may be effective at lower dosages, more selective and effective, having fewer side effects or capable of treating diseases or disorders where resistance to the known compounds has developed.

Chemotherapeutic agents are used for the treatment of infections, cancer, abnormal proliferation disorders (endometriosis, restenosis, psoriasis), and other disorders. Most chemotherapeutic agents have side effects due to lack of specificity. For example, cancer is one of the leading causes of death. One of the primary modes of treating cancer, chemotherapy, is used specifically to limit cell growth and replication. Most chemotherapy agents also affect neoplastic and rapid proliferating cells of normal tissues (e.g., bone marrow, hair follicles, etc.), which results in several negative side effects including hair loss, nausea, vomiting, and suppression of bone marrow function. Moreover, effectiveness of these agents frequently diminishes over time due to the development of resistance.

Resistance to chemotherapeutic agents is even more salient in the treatment of bacterial diseases and fungal diseases. For example, *Helicobacter pylori* causes gastric disorders in large population in the U.S. Lack of effective treatment of such disorders may lead to the development of peptic ulcers, gastritis, dyspepsia and gastric cancer. Another common bacterial disease is periodontal disease, of which the major cause is bacterial plaque, which may lead to the development of periodontitis and eventually to tooth-loss.

It is therefore an object of this invention to provide a new class of compounds effective as anti-infective, anti-proliferative, and anti-inflammatory agents.

It is another object of this invention to provide an effective antineoplastic agent with specific cytotoxicity in order to minimize side effects.

It is a further object of the present invention to provide antiinfective agents which are specific and different from many other drugs currently in use, to provide an alternative method of treatment for drug resistant organisms.

SUMMARY OF THE INVENTION

Natural and synthetic compounds of Formulae Ia, Ib, and Ic having a lactone structure and methods for using and making the compounds and compositions for administration of the compounds have been developed. The compounds are useful as anti-bacterial, anti-fungal and anti-inflammatory agents, and for treating proliferation disorders such as melanoma, leukemia, breast cancer, lung cancer, ovarian cancer, colon cancer, esophagus cancer, liver cancer, and lymphatic cancer. The compounds are also effective for treatment or prevention of inflammatory diseases such as atherosclerosis, lung fibrosis, systemic lupus erythematosus, pancreatitis, sarcoidosis, glomerulitis, and organ transplant rejection. In addition, they are effective for treatment or prevention of bacterial and fungal infections, including treatment of peptic ulcers, gastritis, dyspepsia and gastric cancer, gingivitis and periodontitis.

The method for making a compound of Formulae Ia, Ib, and Ic generally involves: a) providing a precursor having a lactone structure, and b) reacting the precursor with one or more chemical reagents to provide the compound. The compound can be further derivatized by reaction with a nucleophilic agent such as an alcohol, alkoxide, amine, or any other neutral or anionic nucleophiles.

DETAILED DESCRIPTION OF THE INVENTION

I. Lactone Compositions

A. Lactones.

Lactones and their respective derivatives with a hydroxyl in gamma position are disclosed. The lactones and the derivatives thereof can be synthesized or isolated from natural resources. In one embodiment, the lactones and the derivatives can be isolated by means of chromatographic methods, from a plant whose taxonomic scientific name is *Securidaca virgata*, which belongs to Polygalaceae as its botanical family. As used herein, the term "lactones" encompasses any organic chemicals having a five-member ring lactone structure in which the oxygen atom of the C═O group can be replaced by a sulfur atom or a nitrogen grouping. The term "derivatives" as used herein refers to any compounds that are made from the lactones by reacting the lactones with one or more chemical reagents. The term also refers to any products obtainable by ring opening of the lactones with an organic or inorganic nucleophilic agents to form, for example, an acid, ester, amide, or any other products thereof.

In one embodiment, the lactone has the following chemical structure:

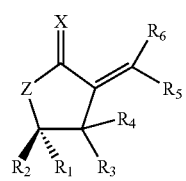

Formula Ia wherein $R_1$-$R_6$ taken independently are a hydrogen atom, a halogen atom, a hydroxyl group, or any other organic groupings containing any number of carbon atoms, preferably 1-8 carbon atoms, and optionally include a heteroatom such as oxygen, sulfur, or nitrogen grouping in linear, branched, or cyclic structural formats, representative $R_1$-$R_6$ groupings being H, alkyl, substituted alkyl, allyl, substituted allyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, alloxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, C1-C20 cyclic, substituted C1-C20 cyclic, heterocyclic, substituted heterocyclic, aminoacid, peptide, or polypeptide group;

Z is a heteroatom such as oxygen, sulfur, or nitrogen grouping in linear, branched, or cyclic structural formats; and X is a heteroatom such as oxygen, sulfur, or nitrogen grouping in linear, branched, or cyclic structural formats.

In another embodiment, the lactone has the following chemical structure:

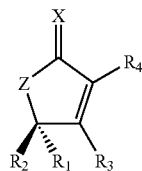

Formula Ib wherein $R_1$-$R_4$ taken independently may be a hydrogen atom, a halogen atom, a hydroxyl group, or any other organic groupings containing any number of carbon atoms, preferably 1-8 carbon atoms, and optionally include a heteroatom such as oxygen, sulfur, or nitrogen grouping in linear, branched, or cyclic structural formats, representative $R_1$-$R_4$ groupings being H, alkyl, substituted alkyl, allyl, substituted allyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, alloxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, C1-C20 cyclic, substituted C1-C20 cyclic, heterocyclic, substituted heterocyclic, arninoacid, peptide, or polypeptide group;

X is a heteroatom such as oxygen, sulfur, or nitrogen grouping in linear, branched, or cyclic structural formats; and Z is a heteroatom such as oxygen, sulfur, or nitrogen grouping in linear, branched, or cyclic structural formats.

In still another embodiment, the lactones having an alpha-methylene group can have the structure as show below:

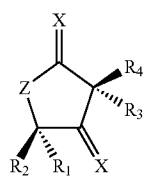

Formula Ic wherein $R_1$-$R_4$ taken independently may be a hydrogen atom, a halogen atom, a hydroxyl group, or any other organic groupings containing any number of carbon atoms, preferably 1-8 carbon atoms, and optionally include a heteroatom such as oxygen, sulfur, or nitrogen grouping in linear, branched, or cyclic structural formats, representative $R_1$-$R_4$ groupings being alkyl, allyl, substituted alkyl, alkenyl, allyl, substituted allyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, alloxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, C1-C20 cyclic, substituted C1-C20 cyclic, heterocyclic, substituted heterocyclic, aminoacid, peptide, or polypeptide group;

Z is a heteroatom such as oxygen, sulfur, or nitrogen grouping in linear, branched, or cyclic structural formats; and X is a heteroatom such as oxygen, sulfur, or nitrogen grouping in linear, branched, or cyclic structural formats.

Representative lactones of formulae Ia, Ib, and Ic are listed in Table I:

TABLE 1

Representative synthetic lactones.

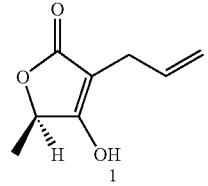
1

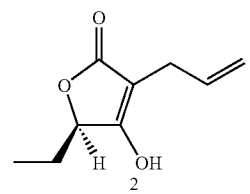
2

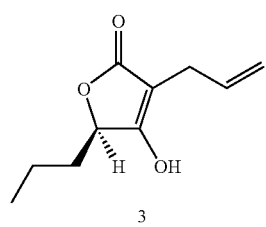
3

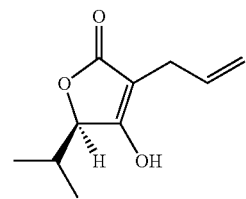
4

TABLE 1-continued
Representative synthetic lactones.
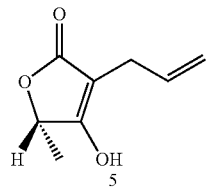
5
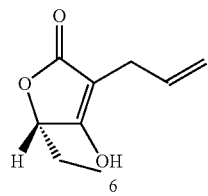
6
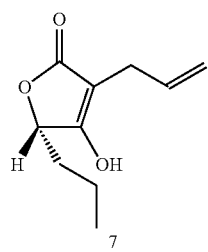
7
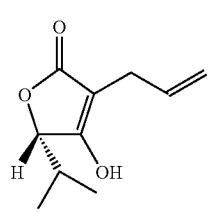
8
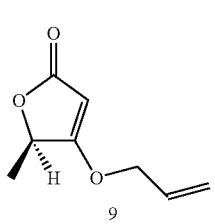
9
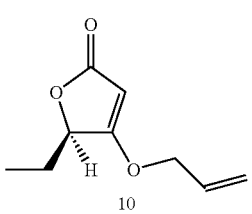
10
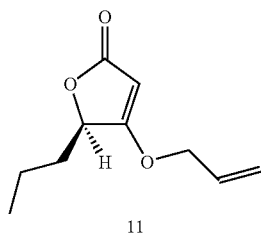
11
TABLE 1-continued
Representative synthetic lactones.
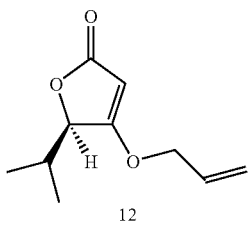
12
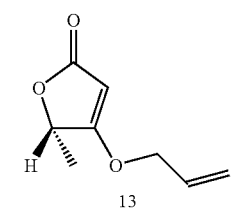
13
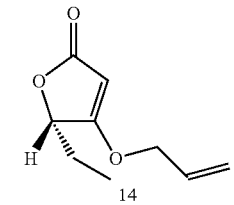
14
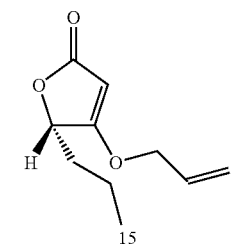
15
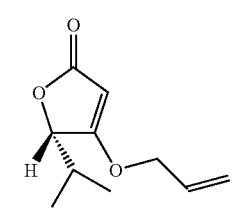
16
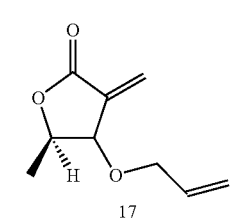
17
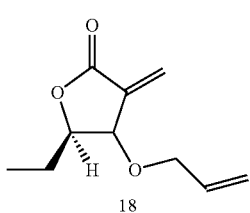
18

TABLE 1-continued
Representative synthetic lactones.
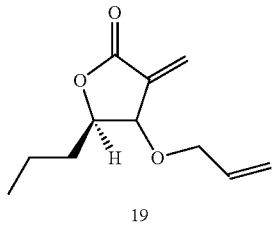
19
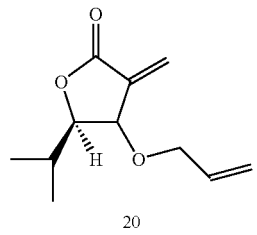
20
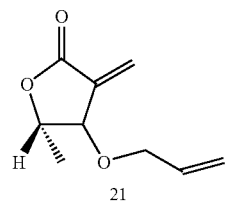
21
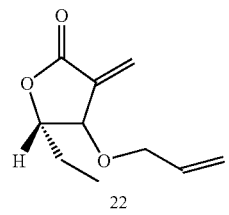
22
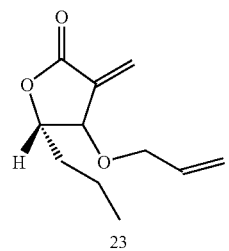
23
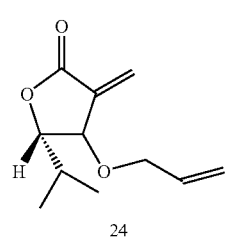
24
TABLE 1-continued
Representative synthetic lactones.
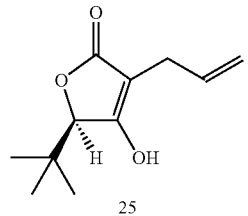
25
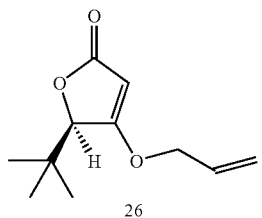
26
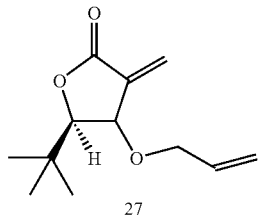
27
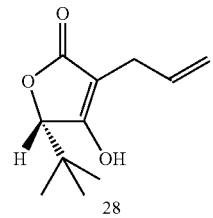
28
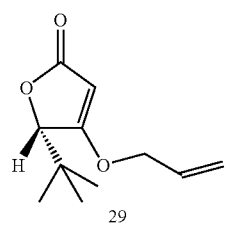
29
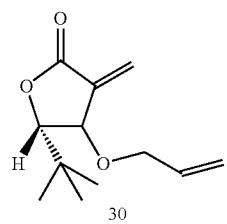
30
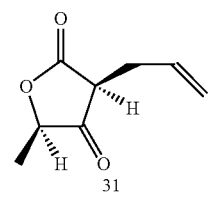
31

TABLE 1-continued
Representative synthetic lactones.
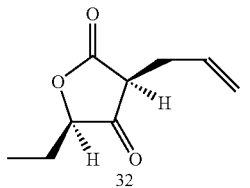
32
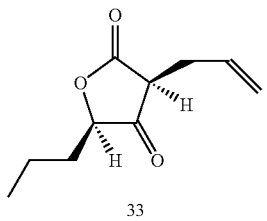
33
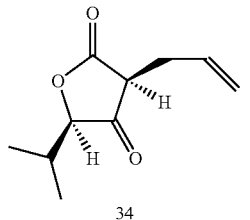
34
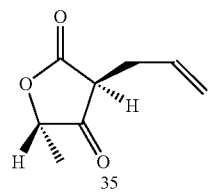
35
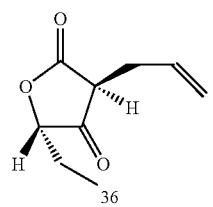
36
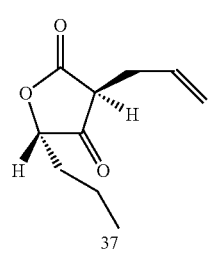
37
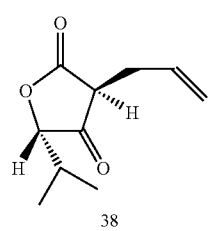
38
TABLE 1-continued
Representative synthetic lactones.
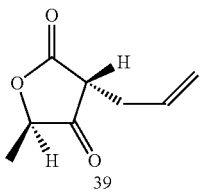
39
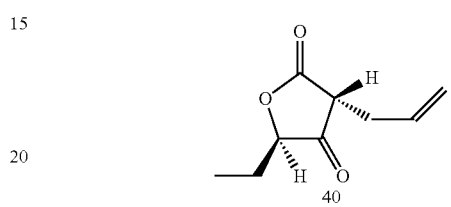
40
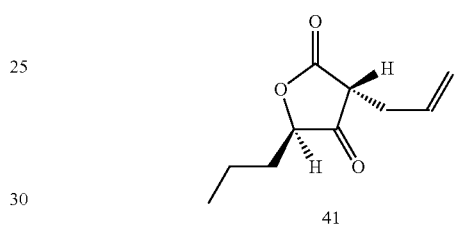
41
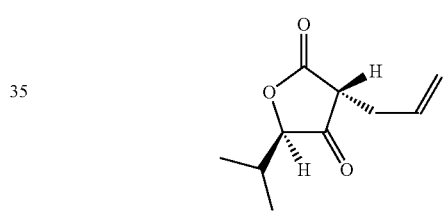
42
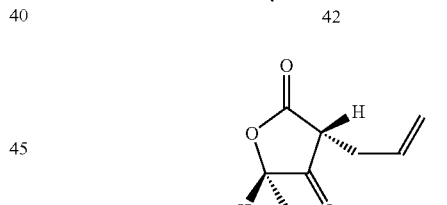
43
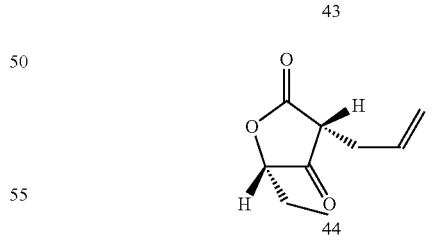
44
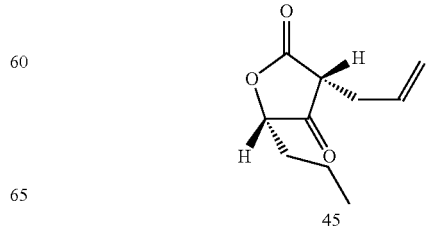
45

TABLE 1-continued

Representative synthetic lactones.

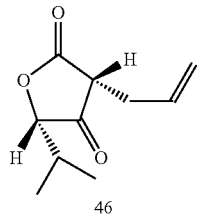

46

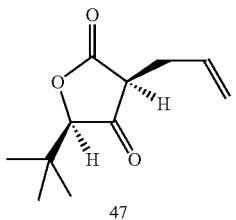

47

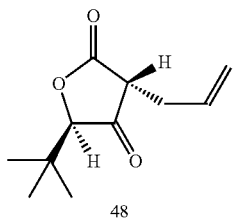

48

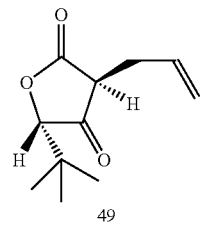

49

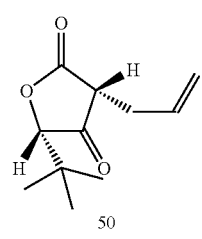

50

The pharmaceutically acceptable acid addition salts of compounds of the formula Ia, Ib, or Ic, may be prepared in a conventional manner by treating a solution or suspension of the free base of the formula 1 with about one chemical equivalent of a pharmaceutically acceptable acid. Conventional concentration and recrystallization techniques can be employed to isolate the salt.

The pharmaceutically acceptable base addition salts of compounds of formula 1 containing an acid group may be prepared in a conventional manner from the acid, e.g. by reaction with about one chemical equivalent of a base.

B. Excipients

The lactone and functional derivatives can be formulated using standard techniques for enteral, parenteral, or topical administration (see, for example, Encyclopedia of Controlled Drug Delivery, Edith Mathiowitz, Ed., John Wiley & Sons, Inc., New York, 1999). Effective dosages can be determined based on the in vitro assays known to those skilled in the art, such as the assays described in the examples.

Suitable pharmaceutically acceptable vehicles for parenteral delivery include sterile saline, phosphate buffered saline, apyrogenic sterile vehicle, and standard microparticulate formulations for injection, including polymeric microspheres, microcapsules, liposomes, and emulsions. These can include degradable polymers such as polylactic acid and polyglycolic acid, and copolymers thereof, polyanhydrides, polyorthoesters, polyhydroxyalkanoates.

Suitable pharmaceutically acceptable carriers include talc, gum Arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

For injection, the lactones will typically be formulated as solutions or suspensions in a liquid carrier.

For topical delivery, the lactone may be formulated in an ointment, creams, lotion, gel, spray, or controlled or sustained release formulation (such as a transdermal patch).

For enteral delivery, the lactone may be formulated in a tablet, capsule, granule, suppository, suspension or solution, dissolved or encapsulated in an excipient such as a sugar like lactose, inert compound such as magnesium stearate, paraffin derivatives, glycols or gum arabic. The formulations may further include dyes, flavorings, preservatives, dispersing or emulsifying agents, or materials modifying release or stability properties of the formulations.

The active compound may be used in combination with a second pharmaceutically acceptable antimicrobial agent, nitroimidazole antibiotics, e.g. tinidazole and metronidazole; tetracyclines, e.g. tetracycline, doxycycline and minocycline; penicillins, e.g. amoxicillin and meziocillin; cephalosporins, e.g. cefaclor, cefadroxil, cephadrine, cefuroxime, cefuroxime axetil, cephalexin, cefpodoxime proxetil, ceftazidime and cefatriaxone; carbapenems, e.g. imipenem and meropene-m; aminoglycosides, e.g. paromomycin; macrolide antibiotics, e.g. erythromycin, clarithromycin and azithromycin; lincosamide antibiotics, e.g. clindamycin; rifamycins, e.g. rifampicin; and nitrofurantoin.

Combinations of the compounds with a pharmaceutical acid-lowering agent may used in the treatment of acid-related disorders, such as acid pump inhibitors, e. g., omeprazole and lansoprazole, or $H_2$ antagonists, e.g., ranitidine, cimetidine, and famotidine.

II. Synthesis of Lactones

The synthesis of the lactones of formulae Ia, Ib, and Ic involves: a) forming an intermediate or precursor having the lactone structure, and b) reacting with the intermediate with one or more appropriate chemical agents to the lactones of formulae Ia, Ib, and Ic.

In one embodiment, the method involves: a) providing a precursor having the following structure:

Formula II

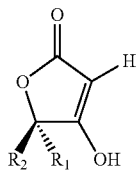

and b) reacting the precursor with one or more appropriate chemical reagents to provide a lactone product of formula Ia, Ib, or Ic (Scheme 1).

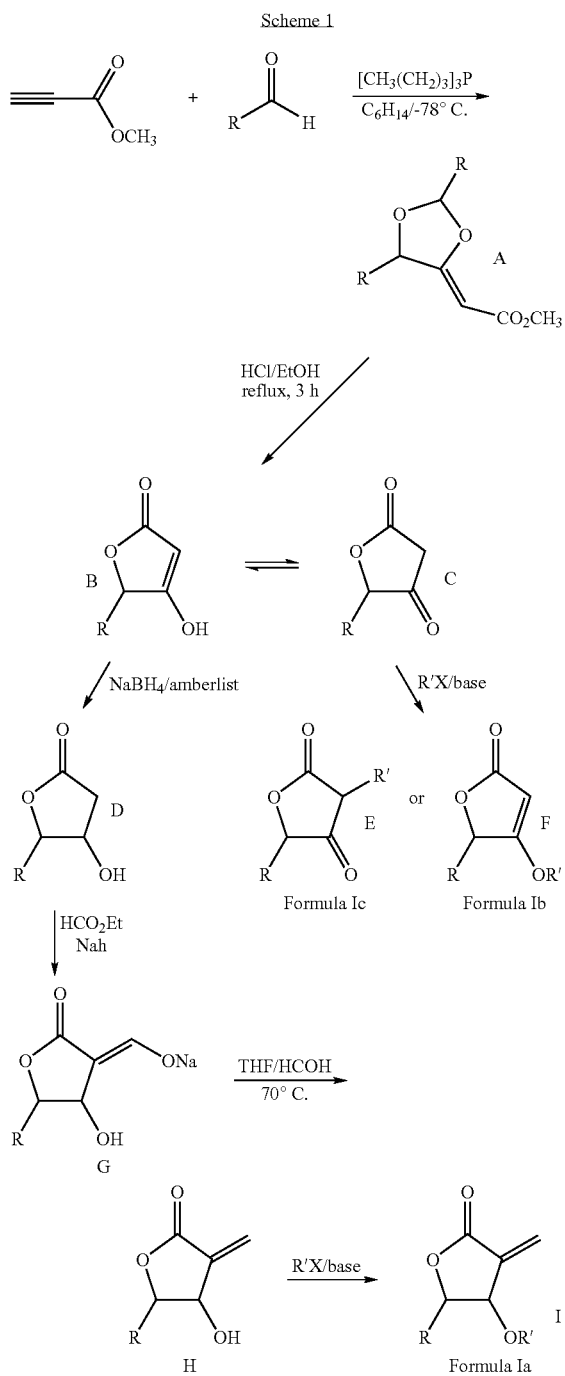

As shown by Scheme 1, an acetylene can react with an aldehyde in the presence of a phosphine, $[CH_3(CH_2)_3]_3P$, to form compound A, which undergoes a ring-rearrangement reaction to form compound B in enolic form. Enolic compound B is in equilibrium with its ketone form, compound C. Reaction of either B or C in the presence of a base such as butyl lithium, sodium carbonate, sodium hydroxide, or sodium methoxide or ethoxide to form compound E (Formula Ic) or F (Formula Ib). In the alternative, the enolic compound B can be subjected to reduction reaction with $NaBH_4$ to form saturated compound D. Compound D undergoes condensation reaction with $HCO_2Et$ to form an exo-cyclic enolate, compound G, which is then reduced by formyl aldehyde to form compound H. Compound H can be readily derivatized to form compound I (Formula Ia) using, for example, an halo alkyl in the presence of a base such as sodium carbonate, sodium hydroxide, or sodium methoxide or ethoxide.

More functionalized lactones can be prepared by readily available synthetic method in the art (see, for example, March, "Advanced Organic Chemistry," 4$^{th}$ Edition, 1992, Wiley-Interscience Publication, New York).

The pharmaceutically acceptable salts of the lactone compounds of the Formulae Ia-c, if in the form of an acid or a base such as an amine, can be prepared in a conventional manner by treating a solution or suspension of the compound of Formulae Ia-c with about one chemical equivalent of a pharmaceutically acceptable base or acid. Conventional concentration and recrystallization techniques are employed in isolating the salt.

III. Methods of Treatment

A. Disorders to be Treated

The lactones are useful as anti-infectives, anti-proliferatives, and anti-inflammatories useful for preventing or treating a broad spectrum of disorders. In particular, the lactones are useful for treating disorders that includes, for example, cancers, gingivitis, periodontitis, a disease caused by *Helicobacter pylori*, diseases caused by bacteria, diseases caused by fungi, and inflammatory diseases.

The lactones can be formulated into fungicidal compositions, antibacterial compositions, anticancer compositions, and anti-inflammatory compositions. Fungicidal compositions are comprised of a fungicidally effective amount of a compound of formulae Ia, Ib, or Ic or a salt thereof and an inert pharmaceutical carrier. The fungicidal compositions are useful particularly on *Saccharomyces cerevisiae, Candida albicans* and other *Candida* such as *Candida glabrata, krusei, tropicalis, pseudotropicalis* and *parapsilosis*, on *Aspergillus fumigatus, Aspergillusflavus, Aspergillus niger, Cryptococcus neoformans, Microsporum canis, Trichophyton rubrun, Trichophyton mentagrophyte* and to combat particularly digestive, urinary, vaginal or *cutaneous candidosis, cryptococcosis*, for example, neuromeningeal, pulmonary or *cutaneous cryptococcosis*, bronchopulmonary and pulmonary aspergillosis and invasive aspergillosis of the immunodepressive system. The compositions can also be used in the prevention of mycotic affections in congenital or acquired immunological suppressions.

The lactones can be administered to treat or prevent inflammatory diseases. Representative inflammatory diseases include artherosclerosis, lung fibrosis, systemic lupus erythematosus, pancreatitis, sarcoidosis, glomerulitis, and organ transplant rejection such as kidney transplant, liver transplant, lung transplant, and heart transplant.

The lactones can also be administered to treat proliferative disorders, including cancers. Representative types of cancers which have shown inhibition in cell growth or proliferation include melanoma, leukemia, breast cancer, lung cancer, ovarian cancer, colon cancer, esophagus cancer, liver cancer, and lymphatic cancer. Other types of abnormal proliferative disorders that the lactones may be useful in the treatment of include endometriosis and restenosis, caused by abnormal overproliferation of endothelial tissue following angioplasty.

The antibacterial compositions can be administered to treat or prevent bacterial disorders, which include, for example, diseases caused by *Helicobacter pylori* such as peptic ulcer disease, gastritis, dyspepsia, and gastric cancer. The antibacterial composition useful for treating or preventing diseases caused by *H. pylori* may be used in combination with a second pharmaceutically acceptable antimicrobial agent or a pharmaceutically acceptable acid-lowering agent.

The lactone antibacterial composition are useful for treating or preventing oral diseases such as periodontitis, plaque, and gingivitis. The composition is effective against the specific anaerobic gram negative organisms associated with gingivitis. The lactone composition can be dissolved in an oral vehicle in the form of oral formulation for topical administration to the oral cavity of an animal. The oral formulation can be in the form of, for example, mouthrinse or dentifrice. The lactone composition can be also formulated into an oral composition for improving oral hygiene by topically applying the lactone composition to the oral cavity.

B. Dosages

The effective amount will be determined based on the disease or disorder to be treated, the mode of administration and the formulation. Effective dosages can be routinely determined based on the effective dosages determined using in vitro assays such as those described in the examples.

The high activity of 4,5-dihydro-3-methylene-2[3H]furanone ("Securolide" or "LMSV-6"), a type of alpha methyl lactone, against *Escherichia coli, Klebsiela pneumoniae, Pseudomona aeroginosa, Staphyloccus aureus*, and its low molecular weight are very beneficial. Advantages of Securolide include its facility and speediness to promote pharmacologic response; its possibility to cross over cellular membrane barriers, where high molecular weight is the main hindrance, and its potent activity against *Pseudomonas*, which is one of the more drug resistant microorganisms.

The method for combating fungal infections comprises administering a fungicidally effective amount of a compound of formula I or an acid addition salt thereof by buccal, rectal, parental route, or by local route as a topical application on the skin and mucous membranes, but the preferred route is the buccal route. The usual daily dose is 1 to 5 mg/kg depending on the method of administration, the condition treated and the specific compound.

The compounds may be administered alone, but will generally be administered in admixture with a pharmaceutical carrier selected with regard to the intended route of administration and standard pharmaceutical practice. For example, they can be administered orally or in the form of tablets containing such excipients as starch or lactose, or in capsules either alone or in admixture with excipients, or in the form of elixirs or suspensions containing flavoring or coloring agents. In the case of animals, they are advantageously contained in an animal feed or drinking liquid in a concentration of about 5 to 5000 ppm, preferably about 25 to about 500 ppm They can be injected parenterally, for example, intramuscularly, intravenously or subcutaneously. For parenteral administration, they are best used in the form of a sterile aqueous solution which can contain other solutes, for example, enough salt or glucose to make the solution isotonic. In the case of animals, compounds can be administered intramuscularly or subcutaneously at dosage levels of about 0.1 to about 50 mg/kg/day, preferably about 0.2 to about 10 mg/kg/day given in a single daily dose or up to 4 divided doses.

The compounds can be administered to humans for the treatment of *H. pylori* infections by either the oral or parenteral routes and may be administered orally at dosage levels of about 0.1 to about 50 mg/kg, advantageously about 0.5 to 50 mg/kg/day given in a single dose or up to 4 divided doses. For intramuscularly or intravenous administration, dose levels are about 0.1 to about 100 mg/kg/day, preferably about 0.5 to about 50 mg/kg/day. While intramuscularly administration may be a single dose or up to 4 divided doses, intravenous administration can include a continuous drip. Variations will necessarily occur depending on the weight and condition of the subject being treated and the particular route of administration chosen as will be known to those skilled in the art.

The second antimicrobial agent and the acid-lowering agent may be administered with the compounds in the same manner as discussed above for the compounds of the invention. Thus, depending on the particular agent, administration may be orally at about 0.1 to about 500 mg/kg, for instance at about 1 to 3 grams per day of second antimicrobial agent, and about 40 to 80 mg per day of the acid-lowering agent, or by injection at about 0.1 to about 200 mg/kg/day.

C. Mode of Administration

The lactone composition can be administered to a warm-blood animal in any suitable mode of administration. The mode of administration can be local administration or systemic administration. The mode of administration may vary with the disorder to be treated or prevented.

The composition can be administered to an animal via enteral, parenteral, or topical administration. Representative modes of administration include: oral administration, nasal administration, pulmonary administration, vaso-injection, subcutaneous injection, transdermal administration, mucosal administration, and administration via buccal, rectal, or vaginal route.

The present invention will be further understood by reference to following non-limiting examples.

EXAMPLE 1

Microbiological Sensitivity Assays

Culture Medium:

Solvent: Buffer Phosphate 0.1N pH=8.0

Antibiotic: LMSV-6 (Securolide):

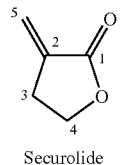

Securolide

Medium coat: 2 mL/100 mL of Medium

Inoculum: 4 mL/Petri Dish

Preparation of Culture Medium:

| Culture Medium for *Staphylococo aureus* (USP 23 <81>) | |
|---|---|
| Peptone | 1.0 g |
| Digestive pancreatic Caseine | 4.0 g |
| Yeast Extract | 3.0 g |

-continued

| | | |
|---|---|---|
| Beef Extract | 1.5 g | |
| Dextros | 1.0 g | |
| Agar | 15.0 g | |
| Water to make about | 1.0 Lit | |
| pH after sterilized 6.6 ± 0.1 | | |
| Culture Medium for *Pseudomona aeroginosa* (USP 23 <81>) | | |
| Pancreatic digestive Caseine | 17.0 g | |
| soy Papaine digestive | 3.0 g | |
| Sodium Chloride | 5.0 g | |
| Dibasic Potassium Phosphate | 2.5 g | |
| Dextrose | 2.5 g | |
| Agar | 20.0 g | |
| Water to make about | 1.0 Lit | |
| pH after sterilized 7.2 ± 0.1 | | |
| Culture Medium for *E. coli* and *k. neumoniae* (according to USP 23 <81>) | | |
| Peptone | 5.0 g | |
| Yeast Extract | 1.5 g | |
| Beef Extract | 1.5 g | |
| Sodium Chloride | 3.5 g | |
| Dextrose | 1.0 g | |
| Dibasic Potassium Phosphate | 3.68 g | |
| Monobasic Potassium Phosphate | 1.32 g | |
| Water To make about | 1.0 L | |
| pH after sterilized 7.0 ± 0.05 | | |

Antibacterial Activity Assays (Minimum Inhibitory Concentration, MIC)

(MIC) Test No. 1

Methodology: Poured in plate, medium Mueler Hinton pH=8

Buffer pH=8 for ceftriaxone pattern dilution

TWEEN™ 20 at 2% for sample dilution

Used Microorganism: *Sarcina lutea*

Sample(S): LMSV-6 (5 pure μL applied to sensibility disc)

Pattern (P): Ceftriaxone (disc with 10 μg)

| P (mm) | S (mm) | |
|---|---|---|
| 12 | 40 | |
| 15 | 44 | $X = 127 \times 100 = 295.35\%$ (with regard to 10 μg of ceftriaxone) |
| 16 | 43 | |
| 43 | 127 | |

Sample Zone of inhibition were three times bigger than pattern.

(MIC) Test No 2

Methodology: Poured in plate, medium Mueler Hinton pH=8

Buffer pH=8 for ceftriaxone pattern dilution

Tween 20 at 2% for sample dilution

Used Microorganism : Sarcina lutea

Sample (S): 16.0 microliters/100 mL and 10 μL applied to sensibility disc

Pattern (P): Ceftriaxone (disc with 10 μg)

| P (mm) | S (mm) |
|---|---|
| 18 | 20 |
| 16 | 23 |
| 15 | 19 |
| 49 | 62 |

$$X = \frac{62 \times 100}{49} = 126.53\% \text{ (with regard to 10 μg of ceftriaxone)}$$

(MIC) Test No. 3

Methodology: Poured in plate, medium Mueler Hinton pH=8

Buffer pH=8 for ceftriaxone pattern dilution

Tween 20 al 2% for LMSV-6 (Securolide) dilution

Used Microorganism: *Sarcina lutea*

Sample (10 microliters/10 mL and 20 μL applied to sensibility disc)

Pattern (P): Ceftriaxone (disc with 10 μg)

| P (mm) | S (mm) |
|---|---|
| 18 | 3 |
| 16 | 3 |
| 15 | 4 |
| 49 | 10 |

$$X = \frac{10 \times 100}{49} = 20.4\% \text{ (with regard to 10 μg of ceftriaxone)}$$

| | |
|---|---|
| 49 | 10 |

$$X = \frac{10 \times 100}{49} = 20.4\% \text{ (with regard to 10 μg of ceftriaxone)}$$

There was not significant zone of inhibition, therefore, the Minimum Inhibitory Concentration (MIC) is too close to 0.2 μL of LMSV-6

| Applied Volume to Disc | Zone of Inhibition |
|---|---|
| 5 μL | 42.0 mm |
| 1.6 M | 20.0 mm |
| MIC is 0.2 μL of LMSV-6 | 3.3 mm |

Results and Discussion

Rats were infected in surgery, and allowed to develop the infection and then successfully treated with Securolide. The high activity of these lactones against *Escherichia coli, Klebsiela pneumoniae, Pseudomona aeroginosa, Staphylococo aureus*, among others, and its low molecular weight, are advantageous. The tests clearly show that Securolide possesses high activity against *Pseudomona*, which is one of harder microorganisms to eliminate.

EXAMPLE 2

Determination of Anti-Fungal Activity

Materials and Methods:

Female mice weighing 18 to 22 g were used and a quantity of *Candida Albicans* 44858 was administered into a vein in the tail at the rate of $10^6$ CFU per mouse (CFU: colony forming unit). The mice were separated into 5 batches of 5 mice and they were treated in the following manner:

One Hour After Infection group 1: the mice were treated with product at 25 mg/kg orally, group 2: the mice were treated with product intraperitoneally at the dose of 25 mg/kg, group 3: the mice were treated orally with Ketoconazole at 25 mg/kg, group 4: the mice were treated intraperitoneally with Ketoconazole at a dose of 25 mg/kg, group 5: the mice did not receive any anti-fungal treatment.

The dead mice were counted over a period of 22 days.

Results and Discussion

The activity of product was excellent at the dose used in the two administration methods. The same treatments were also effective in the "topical model" with dermal fungi, for example trichophyton, and in the sublethal model.

Minimal Inhibitory Concentration (MIC)

*Candida albicans* cells were prepared as indicated in the J. Antimicrobial Chemotherapy, 38, 579-587 and were washed 3 times with a 0.1 M phosphate solution and used immediately to determine the minimal inhibitory concentration (MIC). The MICs were determined by modification of a microtiter plate according to the standard method of the laboratory clinical standards of the Comite National.

RPMI-1640 and L-glutamine were buffered at pH 7 with a 0.15 M solution of MOPS (3-[N-morpholino]propane sulfonic acid). *Candida albicans* cells ($1.5 \times 10^3$ cells/ml) were added to the wells of a 96-well plate containing RPMI-1640 and dilutions of anti-fungal agents. The results were read 48 hours after incubation at 35° C. and the MIC or the minimal inhibitory concentration which inhibited the growth of the *Candida albicans* cells was determined.

Minimal Fungicidal Concentration

After reading the MIC at 48 hours, the plates were shaken and 10 μl of well aliquot was removed from the wells which was placed on rectangular disks containing dextrose sugar. The plates were incubated for 48 hours at 35° C. and the minimal fungicidal concentration and the concentration of the antifungal agent at which there were no number of colony forming units.

EXAMPLE 3

Cytotoxicity or Antineoplasticity Assays

Quantitation of the antiproliferative and cytotoxic effects of drugs can be performed using the tetrazolium salt, MTT (3-(4,5-dimethylthiazol-2-yl)-2,5-diphenyl tetrazolium bromide). In this colorimetric assay, the yellow tetrazolium salt, MTT, is cleaved into purple formazan by the mitochondrial enzyme, Succinate-Dehydrogenase, only in living cells. Formazan accumulates within the viable cells because it is impermeable to the cell membrane. The amount of formazan produced is proportional to the amount of living cells following drug treatment. This assay was used to detect the cytotoxic or antineoplastic effects of our compound against a number of cancer cell lines.

Former methods utilize well known tissue culture techniques using various cancer cell lines, e.g. HEP-2(Laringeal carcinoma), HELA (Cervix Carcinoma). The Formazan concentration is measured in a gradient of Securolide concentrations by multi-well scanning spectrophotometer (ELISA reader). Subsequent data statistic treatment permits one to establish the Inhibitory concentration fifty ($IC_{50}$) which is a quantitative parameter of antineoplastic activity.

Methods and Materials

Materials:

Culture Medium (DMEN+all)

EDTA (Quelant Agent to trap Ca++/Mg++ ions present in cellular membrane, in order to facilitate cellular membrane detachment from plate

TRYPSIN-EDTA

DMEM+ALL AND 10% TERNERO RECENTAL SERUM.

Dimethyl Sulfoxide (DMSO, inert solvent)

MTT [3-(4,5-dimethyltiazol-2-yl)-2,5-diphenyl tetrazolium bromide]

Multiwell scanning spectrophotometers (ELISA readers)

Antineolplasticity Assay

Assessment of cell growth inhibition was determined according to the methods of Skehan et al., J. Nat. Cancer Inst. 82:1107 (1990). Cells were plated between 400 and 1200 cells/well in 96 well plates and incubated at 37° C. for 15-18 h prior to drug addition to allow attachment of cells. Compounds tested were dissolved in 100% DMSO and further diluted in RPMI-1640 containing 10 mM HEPES. Each cell line was treated with 10 concentrations of compounds (5 log range). After a 72 hour incubation, 100 ml of ice-cold 50% TCA was added to each well and incubated for 1 h at 4° C. Plates were then washed 5 times with tap water to remove TCA, low-molecular-weight metabolites and serum proteins. Sulforhodamine B (SRB) (0.4%, 50 mL.) was added to each well. Following a 5 min incubation at room temperature, plates were rinsed 5 times with 0.1% acetic acid and air-dried. Bound dye was dissolved with 10 mM Tris Base (pH 10.5) for 5 min on a gyratory shaker. Optical density was measured at 570 nm.

Data were fitted with the Sigmoid-Emax Concentration-Effect model (see Holford, N. H. G.: Scheiner, L. B., "Understanding the dose-effect relationship: Clinical applications of pharmacokinetic-pharmacodynamic models," Clin. Pharimiacokin 6:429-453 (1981) with non-linear regression, weighted by the reciprocal of the square of the predicted response. The fitting software was developed by the Roswell Park Institute with Microsoft FORTRAN, using the Marquardt algorithm (see Marquardt, D. W., "An algorithm for least squares estimation of nonlinear parameters", J. Soc. Ind. Appl. Math. 1963, 11, 431-441) as adopted by Nash (see Nash. J. C., "Compact numericsal method for computers: Linear algebra and function minimization," John Wiley & Sons, New York, 1979) for the non-linear regression. The concentration of drug which resulted in 50% growth inhibition ($IC_{50}$) was calculated.

EXAMPLE 4

In Vitro Cytotoxicity of LMSV-6 Against Cervical and Prostate Cancer Cells

Four tumor cell lines, including human prostate cancers PC-4 (androgen-insensitive) and LnCaP (androgen-insensitive) and human cervical cancers CaSKi (human papilloma virus—(HPV) Type-16 positive] and C-33 (HPV-negative), were cultured in RPMI-10% bovine serum, glutamine and antibiotics at 5% $CO_2$ an 37 degrees Celsius.

The cytotoxicity of LMSV-6 (tested at 1-1000 μg/mL or 10.2-10,200 μM) was noted after 4 hours for C-33 ($LD_{50}$=538 μM) but not for the others ($LD_{50}$>1,982 μM). There was anti-proliferative activity against all cell types in the presence of LMSV-6 at concentrations of $1\times10^{-2}$ to $10^2$ μM) after 72 hours. The lethal dosages for each cell line is listed below:

| Cell | $LD_{50}$ (μM) |
|---|---|
| C-33 | 7.10 |
| LNCaP | 26.5 |
| PC-4 | 59.2 |
| CaSKi | 64.3 |

Generally, methotrexate, doxorubicin, and paclitaxel ($LC_{50}$=0.1 μM) inhibited the proliferative activity of all cancer types at concentrations of less than 0.001 to 0.5 μM. The only exception was methotrexate, which lacked activity against CaSKi.

Tamoxifen was found to be cytotoxic against all four cell types (measured $LD_{50=34.5}$-79.7 μM, as compared to the expected 50 μM). The curves representing percent inhibition of proliferation of 1000 μg LMSV-6 and 1000 μM tamoxifen were similarly shape and parallel, with tamoxifen being 1.53 times as potent as LMSV-6 ($LD_{50=345}$ μM and 528 μM, respectively).

EXAMPLE 5

Activity Against *Helicobacter pylori*

Agar Dilution of Antimicrobial Compound 6 mg of the compound to be evaluated was dissolved in 0.6 ml 100% dimethylsulfoxide (DMSO) and then brought up to 6 ml with sterile brucella broth and the solubility was noted. The final concentration of DMSO is 10% of the total volume. Serial 2-fold dilutions (3 mL Securolide+3 mL brucella broth) were then made in sterile brucella broth. A 2 mL aliquot of each broth dilution within the series was placed in separate sterile Petri dishes, to which 18 ml of melted and cooled (approx. 50° C.) brucella agar supplemented with 7% horse blood was added. This yielded a final 1:10 dilution of Securolide in agar, and a final concentration of DMSO of 1%. For example, if the highest concentration of drug in agar is 100 μg/mL. Agar plates were prepared one day prior to inoculating, and refrigerated overnight.

Inocula Preparation

*Helicobacter pylori* cultures were maintained on trypticase soy-5% sheep blood agar plates, and were transferred every 48 hours. *Helicobacter mustelae* cultures were maintained on the same agar transferred every 48-60 hours, depending upon the extent of the growth of the previous transfer. Plates were incubated at 37° C. in GasPak jars with water-activated (10 ml) CampyPak Plus (BBL Microbiol. Systems) envelopes with palladium catalyst.

*Helicobacter* cultures were grown in brucella broth supplemented with 10% fetal calf serum in 10 ml volumes in deep Petri dishes. The plates were incubated for 18-20 hours at 37° C. in GasPak jars with water-activated (10 ml) CampyPak Plus envelopes with palladium catalyst on a shaker at 50 rpm.

Overnight cultures (approx. $10^8$ CFU/mL) were diluted 10-fold in brucella broth (no FCS) in screw-capped tubes for use as the standard inoculum. The wells of a Steer replicator were filled with 0.8 mL of the diluted organism, and approximately $2\times10^4$ cells in 0.002 ml were placed on the agar surface. Inoculated plates were placed in a GasPak jar to which water-activated (10 mL) Campy Pak Plus envelopes with palladium catalyst were added, and incubated at 37° C. for 48 hours.

Results and Discussions

Following incubation, all test plates were compared to a Securolide-free growth control plate. The MIC is the concentration which inhibits growth compared to the control plate. A thin film of growth that might be visible at higher concentrations was discounted, and not considered the true MIC. Control organisms were also inoculated on each plate, and diluted 1000-fold for use as inocula. The control organisms include *Campylobacter jejuni*, and the screening cultures of *E. Coli* [ATCC 35218, Lote 202602, Exp 05/2000 (19-258)]. *Pseudomona aeroginosa* [ATCC 27853, Lote 202992, Exp 08/2000 (19-060)], *E. Cloacae, Providencia stuartii* and *P. rettgeri*. Plates and/or inocula transfers should not be out of the microaerophilic environment longer than 2 hours. All manipulations involving *Helicobacter* cultures were performed in a laminar flow hood to decrease the chance of contaminating the cultures with mold.

The mouse model of Lee et al., Gastroenterology, 99:1315-23 (1990) was used to predict the in vivo activity of a compound against *H. Pylori* in humans. *Helicobacter felis* was grown in brucella broth with 10% fetal bovine serum. A frozen culture was quickly thawed; the culture was checked for motility, and 0.5 cc of the thawed frozen culture was inoculated into a deep tissue culture dish containing 9.5 cc of the brucella/serum mix. The dishes were put into a Capy Pak jar [BBL] to insure a microaerophilic atmosphere. The jar was put on a rotary shaker at 60 rpm in a 37° C. incubator. After 18 hours, there should be visible turbidity. The culture was checked for purity and motility under a (phase) microscope and then pooled into a flask. Swiss-Webster female mice (18-20 g) were fasted for 18 hours before infection. The mice were infected three times on alternate days during a single week. Dosing began two weeks after the last dose of organism. Treatments were given once per day for fourteen consecutive days. Sacrifice was performed about three weeks after completion of therapy. For each mouse, the stomach was excised and opened along the greater curvature. A plug (a 3 mm tissue section) was taken from the antrum region of the stomach. The plug surfaced was washed, minced, and dropped into a tube with 100 microliters of urease reagent. The urease reagent (pH 6.3-6.5) contained urea and phenol red. If Helicobacter is present, urease will break down urea producing a change of pH. A purple (alkaline) color indicates positive for Helicobacter; a red/yellow (no change) color indicates negative for Helicobacter. Any color change was recorded after 18 hours. There were usually twenty mice per treatment group; the percent positive for each group was recorded.

There are several methods used clinically to determine whether *Helicobacter pylori* is present in a human subject, which are employed for initial diagnosis of infection prior to treatment, as well as for determining the success of treatment in eradicating the organism from the patient.

The urea breath test involves ingestion of radiolabelled urea. *H. pylori* produces a urease enzyme which degrades urea; mammalian gastric cells do not contain this enzyme. Exhalation of labeled carbon dioxide (analyzed by mass spectrometry or radioactivity, depending on the isotope employed) therefore indicates that *H. pylori* is present.

Serology can also be used to assess infection with *H. pylori*. Detection of serum antibodies to *H. pylori*, such as IgG and IgA, was carried out using enzyme-linked immunosorbent assay (ELISA). Numerous different. *H. pylori* proteins can be employed as antigens.

Endoscopy of the patient provides samples of tissue which can be cultured in a microaerophilic environment to diagnose *H. pylori* infection. Alternatively, the sample can be examined histologically by employing one of a number of stains such as Giemsa or hematoxylin-eosin. A urea test, which again takes advantage of the production of urease by *H. pylori*, can also be applied. This test relies on the formation of ammonia from the urea hydrolysis, which results in an observable change in pH.

EXAMPLE 6

Assay of Activity Against Gingivitis

Evaluation of oral compositions against gingivitis, using a Securolide-containing mouth rinse, performed in a study on 30 beagle dogs for 10 weeks, clearly shows its superior effectiveness against gingivitis. The procedure used includes the complete removal of hard and soft dental deposits, after which the dogs were kept on a soft diet for six weeks to permit the development of gingivitis. The dentitions were then treated with the test solutions twice a day, 5 days a weeks, for about 15 seconds on each side of the mouth. The animals were examined and the degree of inflammation of the gingiva was scored according to a scale of 0 to 3:

0=No inflammation,

1=Mild, localized edema, and redness of gingival margin, no bleeding is elicited upon gentle finger pressure, 2=Moderate edema, and redness of gingival margin with bleeding upon gentle finger pressure, 3=Severe edema and ulceration of gingival margin and attached gingiva, and bleeding without gentle finger pressure. A placebo rinse and 0.5% metronidazole rinse were used as the negative and the positive controls, respectively.

Results and Discussion

Compared to the placebo, Securolide rinses significantly reduced the development of gingivitis. The resultant product is effective in controlling gingivitis and treating periodontitis. In addition, it provides a simple means of improving oral hygiene when used on a regular regime of 1 to 3 applications to the oral cavity per day.

EXAMPLE 7

In Vitro Mutagenic Studies of LSV-6 (Ames Testing)

This study was performed in accordance with the norms of USC 79/831, which establishes the guidelines for toxicological analytical methods.

The Ames test detects drug-induced 'reverting mutations' in previously mutated strains of *Salmonella typhimurium*, all of which have the rfa mutation that makes their cell membranes permeable to chemical agents. Each test strain possesses a known mutation (deletion, substitution or addition of base pairs) in the histidine operon. The presence of these mutations incapacitates the growth of these cells in a histidine-poor culture medium. A 'reverting mutation' by a drug could reverse the effects of any of these mutations, restore the strain to its former histidine-positive status, and hence, increase the growth of *S. typhimurium* in the histidine-poor medium.

A drug is said to be mutagenic if it causes a greater than 2-fold increase in the number of colonies growing in histidine-poor medium. LMSV-6 (at 1 or 10 μg/mL) was added to bacterial strain TA98 and did not increase normal colony count in histidine-poor medium nor did LMSV-6 (at $\leq 100$ μg/mL), added to bacterial strain TA100, therefore meeting the mutagenicity criterion. These preliminary results indicate that LMSV-6 does not revert *S. typhimurium* TA98 or TA100 mutations and should not be expected to cause mutations in the human genome.

EXAXPLE 8

Study of Adverse Reactions to LMSV-6 in Healthy Volunteers

Methods

Nineteen healthy volunteers participated in the study. The age of the participants was between 21 and 40 years with an average of 30.5±7.2 years. The weight was between 150 and 190 pounds with a median of 163.2±14.3 pounds and the height was 1.8 to 2.1 meters with an average of 1.9±0.1 meters. The subjects were selected at random in agreement with the national and international criteria and norms established for investigations with human beings.

The state of health of the participants was established using several clinical evaluations, laboratory tests, electrocardiographs and thoracic radiographs. The functionality of the liver and the renal systems was verified by chemical-enzymatic studies. Likewise, for each participant we carried out tests of blood chemistry, pathology and urinalysis. For the females, the absence of pregnancy and/or lactation was verified by means of laboratory tests and gynecological evaluation.

Participants were divided into three groups selected at random (n=6):

Group I (placebo) received 2.0 ml of saline solution (ClNa$^+$, 0.9%),

Group II, received 60 mg of LMSV-6 intramuscularly, and Group III (n=7) received 100 mg of LMSV-6 intramuscularly. The participants underwent several tests used to establish the basal values of the objective parameters of the analysis, which included:

Lab Studies: hemogram, blood chemistry, urinalysis and coproanalysis

Cardiovascular Function: arterial tension (TA), cardiac rhythm (RC), cardiac frequency (FC) and radial pulse (PR)

Pulmonary Functions: pulmonary respiration (VP) and respiratory frequency (FR)

Renal Function: urinary volume and urinary frequency (FU)

Sensory System: hearing, vision, smell, taste and sensory reflexes

Skin and/or Teguments: sensitivity, skin texture, temperature and musculo-skeletal tone Neurovegetative Functions: salivary gland and sweat gland activities, gastrointestinal mortality and visceral reflexes Hypersensitivity Reactions: local sensitivity and systemic sensitivity.

The evaluations were taken at the following time intervals: Time 0.0, 5.0, 15.0, 20.0, 30.0 and 45.0 min.; 1.0 h., 1.5, 2.0, 3.0, 4.0, 6.0, 8.0, 12.0, 24.0, 36.0 and 48.0 hours.

Results

The reports of the laboratory tests and special exams performed to verify the state of health of the participants showed the values were maintained within the basal levels and there was no observation of any difference with respect to the group that received the placebo.

The results of the laboratory tests performed dealing with the urinary functions and the microbiological pattern found the values to be within the reference values for the utilized methods. Likewise, the results of the copra analysis and they also show no pathological change.

The individual values and averages±standard deviation per group of participants before and during the trials were measured to determine the adverse reaction and margin of tolerance to LMSV-6 with respect to cardiovascular parameters including arterial tension (TA), cardiac frequency (FC), radial pulse (PR) and cardiac rhythm (RC). For healthy volunteers, which received 60 and 100 mg of LMSV-6 and 2 ml of 0.9% sodium chloride as a placebo, the results show that in relation to the basal values and those of the placebo control group, the levels of TA, FC, PR and RC did not change with the treatment. Likewise, there was no variation in the electrocardiograph pattern between the basal conditions and after the study.

The individual values and the averages±standard deviations per group involved in the evaluation of the effects of LMSV with respect to the respiratory functions in healthy volunteers were also measured. The results demonstrate that in relation to the basal values and those of the placebo control group, the treatment in the tested dosages did not alter the respiratory mechanics and dynamics of the participants. The respiratory frequency (FR) was maintained in a range of 18 to 20 respirations per minute during the entire test.

According to that which was observed in the basal conditions and in the placebo group, none of the parameters evaluated dealing with the respiratory dynamic, inspiration, aspiration, tracheal respiration, bronchial respiration and thoracic-pulmonary distension and the superior and inferior airflow, suffered any alteration.

The evaluation of the effects of LMSV-6 with respect to the renal function parameters showed that the values of urinary frequency in individuals of the control group and those which were treated were maintained within a range without much significant variation of 3.1±0.7 to 3.3±1.5 times in a period of 12 hours of direct observation. Likewise, the average urinary volume in the same period was between 434.2±213.2, 489.2±94.3 and 394.3±103.9 ml in the placebo groups and the groups which received 60 and 100 mg of LMSV-6, respectively. This demonstrates that the treatment did not affect the fundamental renal functions.

The data of the effect of LMSV-6 on the mental state and sensory acuteness: auditory, visual, olfactory and taste discrimination indicate that the treatment did not provoke any alteration in any of the functions or analyzed parameters. Likewise, there was not any alteration in the superficial and osteotendinous reflexes.

The data of the evaluation of the effects of LMSV-6 on cutaneous sensitivity and temperature indicate that the treatment did not provoke any change in the cutaneous sensitivity, nor in the temperature of the participants. Likewise, there is no evidence of any alteration in the musculo-skeletal tone of any of the participants of the control groups or the treated groups.

The treatment did not produce any alteration in the texture or moisture of the skin in any of the participants in the study, and there was no change produced in the characteristics of the oral and nasal mucosas due to a treatment effect.

The data dealing with the evaluation of allergic effects (reactivity), both local and systemic, indicate that there was not any manifestation of allergic reactions in any of the participants.

The data of the evaluation and effects of LMSV-6 at a neurovegetative level (glandular and visceral) show that in the ranges of studied dosages (60 and 100 mg), there is no evidence of any manifestation of neurovegetative alteration at the gastrointestinal visceral level, genito-urinary level, larynx-opthalmic glands, nor cardiotonic effect; which is to say, there is no alteration at the level of the exocrine and endocrine glands.

The results of the present study affirm that LMSV-6 possesses an ample margin of tolerance and that the maximum dosage tested (100 mg) was well tolerated by all participants. Likewise, there is no evidence, sign or symptom of adverse reactions in any participants involved in the study.

I claim:

1. A method of treating one or more symptoms of a disorder comprising administering to an animal a composition comprising an effective amount of a compound or a pharmaceutically acceptable salt or hydrate thereof to inhibit cell growth or proliferation associated with the disorder, wherein the compound has one of the following structures:

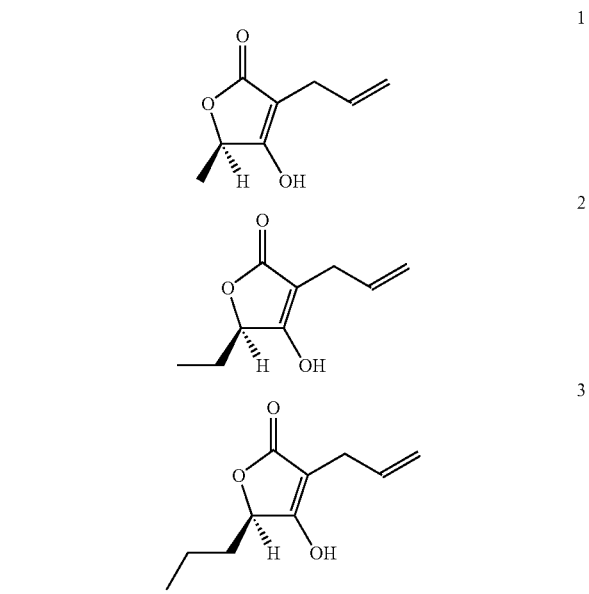

-continued
4
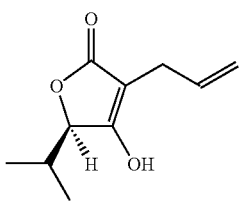
5
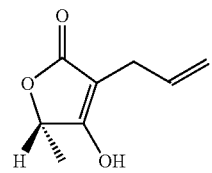
6
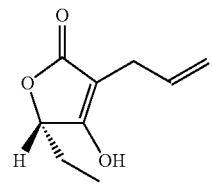
7
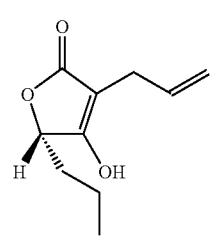
8
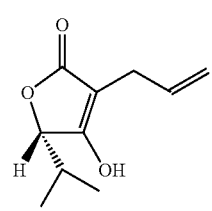
9
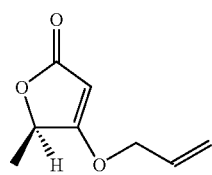
10
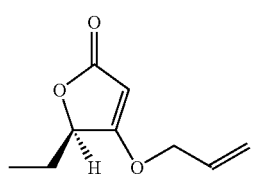
11
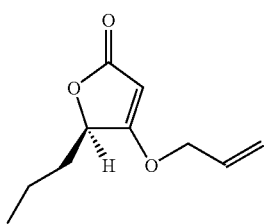
-continued
12
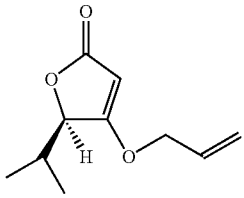
13
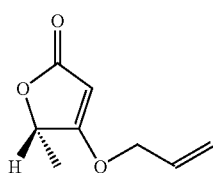
14
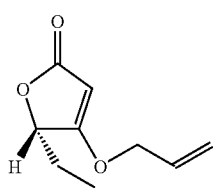
15
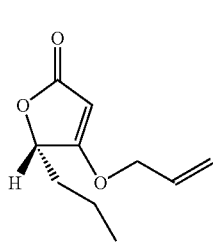
16
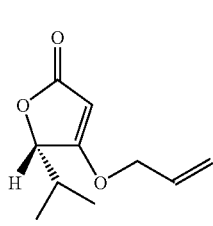
17
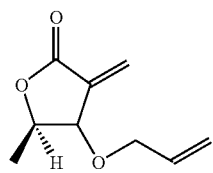
18
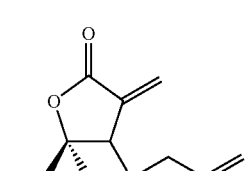
19
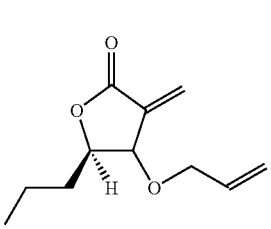

-continued
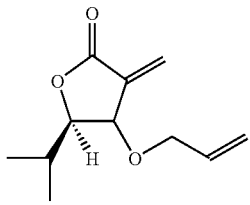
20
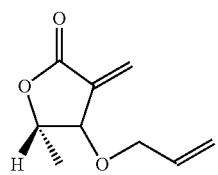
21
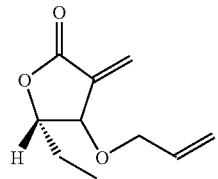
22
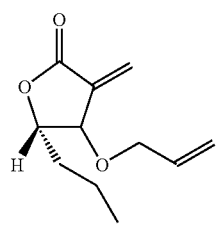
23
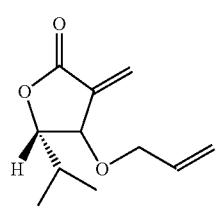
24
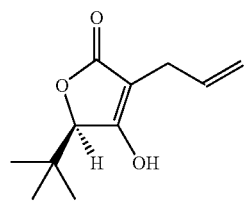
25
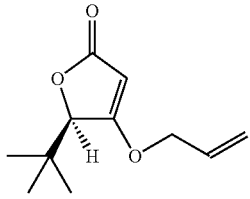
26
-continued
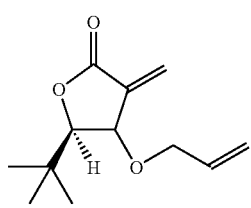
27
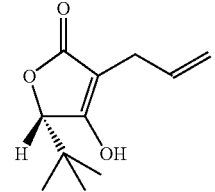
28
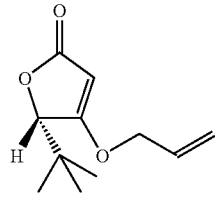
29
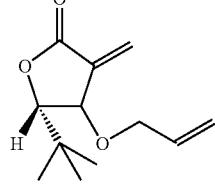
30
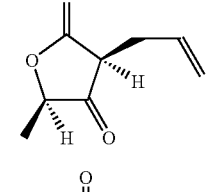
31
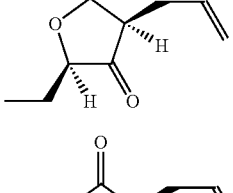
32
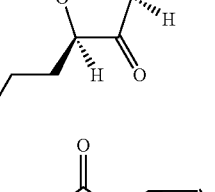
33
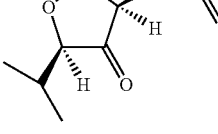
34

-continued

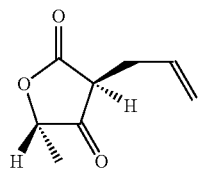
35

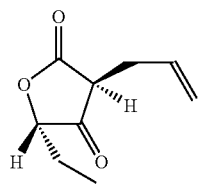
36

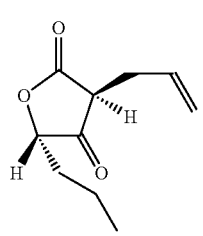
37

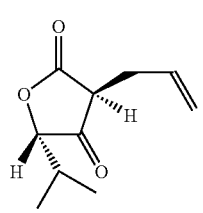
38

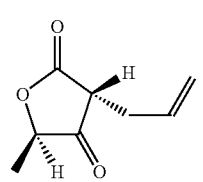
39

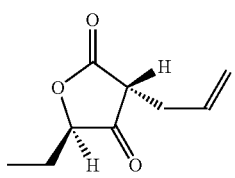
40

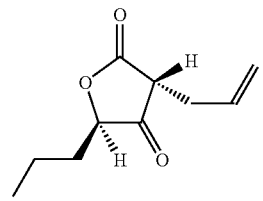
41

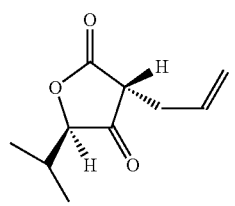
42

-continued

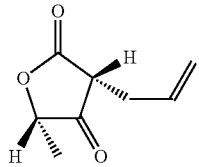
43

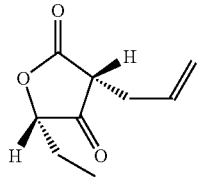
44

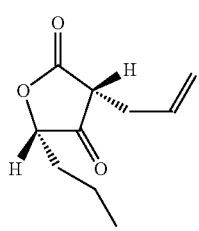
45

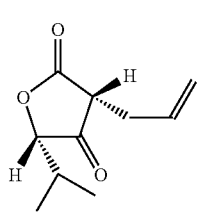
46

2. The method of claim 1 wherein the disorder is selected from the group consisting of melanoma, leukemia, breast cancer, lung cancer, ovarian cancer, colon cancer, esophagus cancer, liver cancer, and lymphatic cancer.

3. A method of treating one or more symptoms of a disorder comprising administering to an animal a composition comprising an effective amount of a compound or a pharmaceutically acceptable salt or hydrate thereof to inhibit cell growth or proliferation associated with the disorder, wherein the compound is an alpha methylene gamma lactone having the chemical formula:

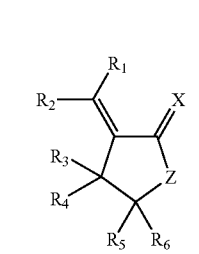

wherein R1-R6 taken independently or R3-R6 taken together are a hydrogen atom or a group or grouping selected from the group consisting of alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, C1-C20 cyclic, substituted C1-C20 cyclic, heterocyclic, substituted heterocyclic, aminoacid, peptide, and polypeptide groups;

Z is a heteroatom selected from the group consisting of oxygen, sulfur, and nitrogen groupings in linear, branched, or cyclic structural formats; and X is a heteroatom selected from the group consisting of oxygen, sulfur, and nitrogen groupings in linear, branched, or cyclic structural formats.

* * * * *